US011096629B2

(12) United States Patent
Harpe et al.

(10) Patent No.: US 11,096,629 B2
(45) Date of Patent: Aug. 24, 2021

(54) BIO-IMPEDANCE SPECTROSCOPY SYSTEM AND METHOD FOR BIO-IMPEDANCE MEASUREMENT

(71) Applicant: Stichting IMEC Nederland, Eindhoven (NL)

(72) Inventors: Pieter Harpe, Eindhoven (NL); Jiawei Xu, Eindhoven (NL)

(73) Assignee: Stichting IMEC Nederland, Eindhoven (NL)

( * ) Notice: Subject to any disclaimer, the term of this patent is extended or adjusted under 35 U.S.C. 154(b) by 620 days.

(21) Appl. No.: 15/247,172

(22) Filed: Aug. 25, 2016

(65) Prior Publication Data
US 2017/0071552 A1 Mar. 16, 2017

(30) Foreign Application Priority Data

Sep. 14, 2015 (EP) .................................. 15184978

(51) Int. Cl.
*A61B 5/00* (2006.01)
*A61B 5/0537* (2021.01)
(Continued)

(52) U.S. Cl.
CPC .......... *A61B 5/7278* (2013.01); *A61B 5/0205* (2013.01); *A61B 5/0537* (2013.01);
(Continued)

(58) Field of Classification Search
CPC ... A61B 5/7278; A61B 5/0205; A61B 5/0402; A61B 5/0428; A61B 5/0537
See application file for complete search history.

(56) References Cited

U.S. PATENT DOCUMENTS 5,063,937 A * 11/1991 Ezenwa ............... A61B 5/0535
600/536
2004/0054273 A1* 3/2004 Finneran ............ A61B 5/04004
600/393

(Continued)

FOREIGN PATENT DOCUMENTS

| DE | 102010039790 A1 * | 3/2012 | ........... A61B 5/0538 |
| EP | 2314217 A1 | 10/2009 | |
| WO | WO-2007054700 A1 * | 5/2007 | ............. G01R 27/26 |

OTHER PUBLICATIONS

Sun, Tao et al., "High Speed Multi-Frequency Impedance Analysis of Single Particle in a Microfluidic Cytometer Using Maximum Length Sequences", Lab on a Chip, vol. 7, 2007, pp. 1034-1040.

(Continued)

*Primary Examiner* — Daniel L Cerioni
*Assistant Examiner* — Yasmeen S Warsi
(74) *Attorney, Agent, or Firm* — McDonnell Boehnen Hulbert & Berghoff LLP

(57) ABSTRACT

The present disclosure is directed to an impedance spectroscopy system for bio-impedance measurement. The impedance spectroscopy system includes a signal generator configured to generate a signal with a broadband frequency spectrum and to generate an analog injection current from the signal with the broadband frequency spectrum. The analog injection current has a high pass frequency characteristic. The impedance spectroscopy system also includes an amplifier configured to measure a voltage signal in response to the analog injection current and to simultaneously measure a biopotential signal. Further, the impedance spectroscopy system includes a processor configured to analyze the voltage signal to derive a bio-impedance spectrum as well as to derive further information from the biopotential signal.

20 Claims, 5 Drawing Sheets

(51) Int. Cl.
*G01N 27/02* (2006.01)
*G01N 33/483* (2006.01)
*A61B 5/30* (2021.01)
*A61B 5/318* (2021.01)
*A61B 5/0205* (2006.01)
*A61B 5/053* (2021.01)

(52) U.S. Cl.
CPC .............. *A61B 5/30* (2021.01); *A61B 5/318* (2021.01); *A61B 5/725* (2013.01); *A61B 5/7225* (2013.01); *G01N 27/026* (2013.01); *G01N 33/4836* (2013.01); *A61B 5/053* (2013.01); *A61B 5/7257* (2013.01)

(56) References Cited

U.S. PATENT DOCUMENTS

| | | | | |
|---|---|---|---|---|
| 2006/0004300 | A1* | 1/2006 | Kennedy | A61B 5/053 600/547 |
| 2007/0276270 | A1* | 11/2007 | Tran | A61B 5/002 600/508 |
| 2008/0045832 | A1* | 2/2008 | McGrath | A61B 5/024 600/427 |
| 2011/0066054 | A1* | 3/2011 | Yazicioglu | A61B 5/04 600/509 |
| 2015/0073295 | A1* | 3/2015 | Gordon | A61B 5/053 600/547 |
| 2015/0119747 | A1* | 4/2015 | Torfs | A61B 5/7207 600/547 |

OTHER PUBLICATIONS

Harpe, Pieter et al., "A 7-to-10b 0-to-4MS/s Flexible SAR ADC with 6.5-to-16fj/Conversion-Step", ISSCC 2012 / Session 27 / Data Converter Techniques / 27.8, Feb. 22, 2012, pp. 472-474.

Yazicioglu, Refet Firat et al., A 60 μW 60 nV/√Hz Readout Front-End for Portable Biopotential Acquisition Systems, IEEE Journal of Solid-State Circuits, vol. 42, No. 5, May 2007, pp. 1100-1110.

Extended European Search Report and Written Opinion, EP Application No. 16188313.7, dated Jan. 13, 2017, 7 pages.

"A 345 μW Multi-Sensor Biomedical SoC with Bio-Impedance, 3-Channel ECG, Motion Artifacat Reduction, and Integrated DSP", Nick Van Helleputte, et al., IEEE Journal of Solid-State Circuits, vol. 50, No. 1, pp. 230-244 (Oct. 14, 2014).

* cited by examiner

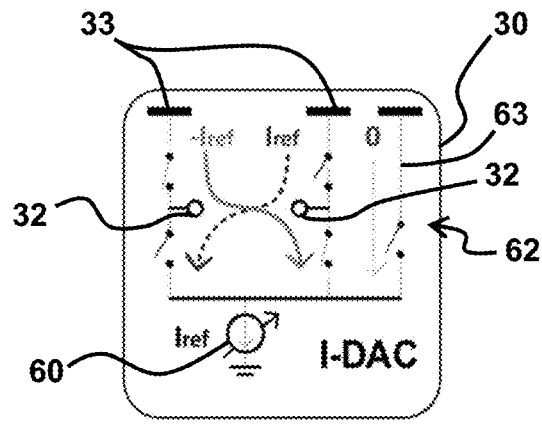
Figure 3
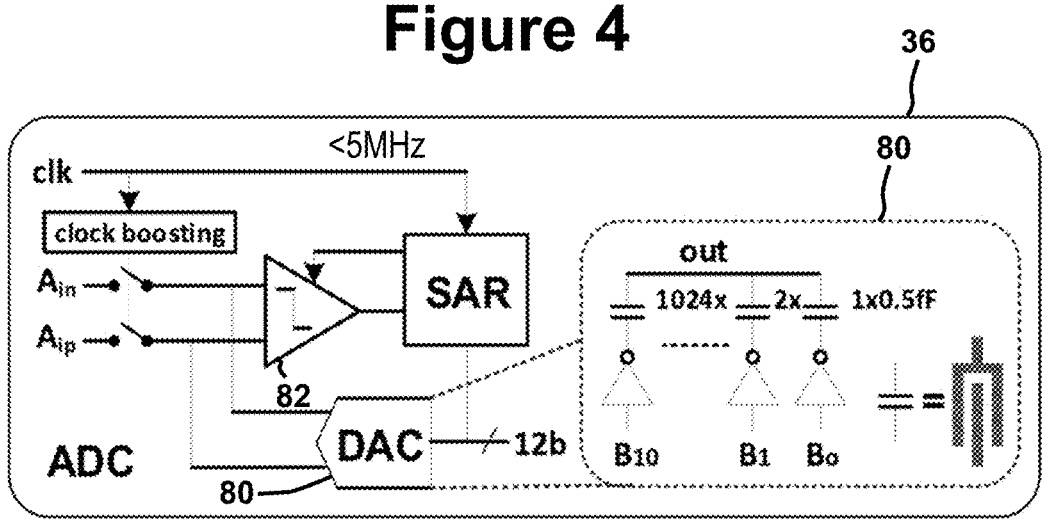
Figure 4
Figure 5

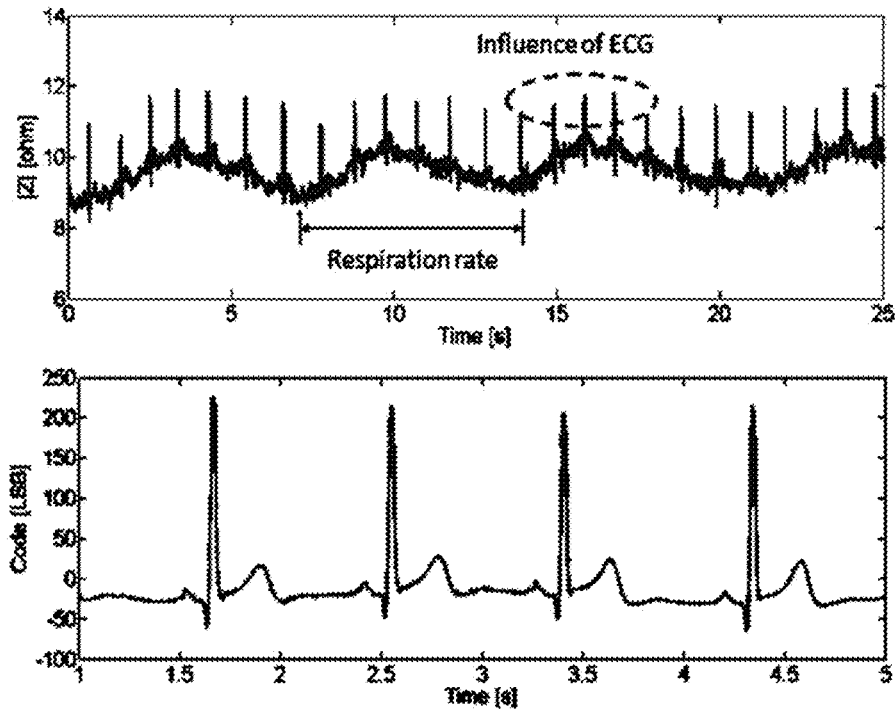
Figure 10
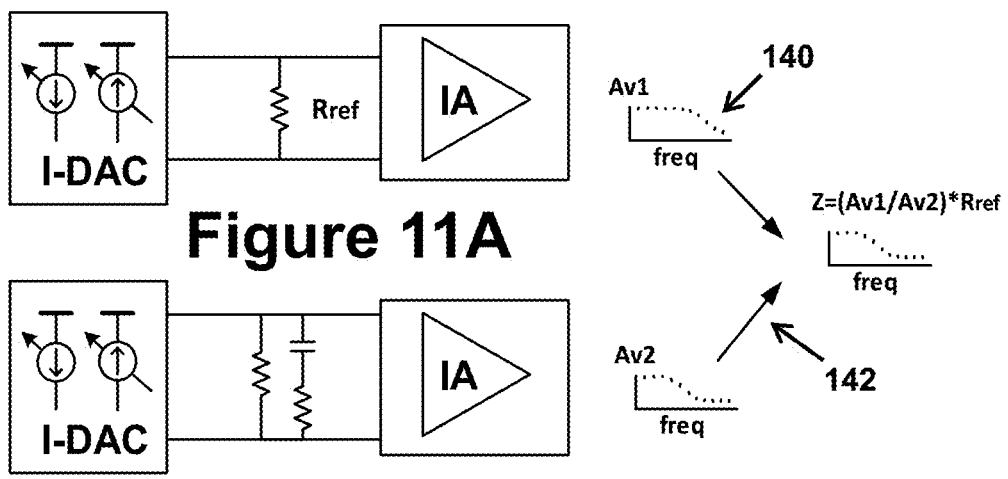
Figure 11A
Figure 11B

US 11,096,629 B2

BIO-IMPEDANCE SPECTROSCOPY SYSTEM AND METHOD FOR BIO-IMPEDANCE MEASUREMENT

CROSS-REFERENCE TO RELATED APPLICATIONS

The present application is a non-provisional patent application claiming priority to European Patent Application No. EP 15184978.3, filed Sep. 14, 2015, the contents of which are hereby incorporated by reference.

FIELD OF THE DISCLOSURE

This disclosure relates to the measurement of bio-impedance, in particular complex bio-impedance values over a broad range of frequencies, in order to implement a spectral bio-impedance analysis.

BACKGROUND

Non-invasive wearable medical devices for lifestyle and healthcare are increasingly being used for monitoring chronic diseases and detecting early health problems. Congestive heart failure (CHF), a chronic heart failure characterized by fluid overload, is one of the major conditions with detrimental effects on quality of life, and potentially fatal.

Bio-impedance analysis (BIA) has been clinically used to track congestive heart failure. By injecting a low-level AC current to a body segment, a voltage proportional to the tissue impedance can be measured. Bio-impedance is used to estimate various physiochemical and physiological states, such as thoracic fluid, respiration, skin hydration and body composition.

Electrocardiography (ECG) is often used as a diagnosis tool of congestive heart failure, by measuring the electrical activity in the heart to detect coronary artery diseases and heart attacks. Therefore, simultaneous measurement of the bio-impedance and ECG can extend the range of extracted biomedical information for improved diagnosis accuracy.

Bio-impedance can be measured at single-frequency (SF), multi-frequencies (MF), or by impedance spectroscopy (IS). Single-frequency measurement may allow for a high signal-to-noise ratio (SNR). However, in order to extract the RC components of a complex bio-impedance network, impedance should be measured at several frequencies.

FIG. 1A shows an equivalent model of the bio-impedance of a cellular organism. The extra-cellular region 10 is modeled by a series (external) resistance Re in a first branch, and the intra-cellular region 12 is modeled by a second branch of cell wall capacitors Cm in series with an (internal) resistance Ri. The two branches are in parallel. FIG. 1B shows the current flowing. A low frequency current 14 flows through the extra-cellular regions and a high frequency current 16 flows through the intra-cellular regions.

State-of-the-art multi-frequency implementations, relying on analog signal processing, where bio-impedance measurement is performed separately at each frequency, can lead to an increased acquisition time. In addition, simultaneous bio-impedance and ECG measurement increases the system complexity and power by using two separate readout circuits.

Impedance spectroscopy (IS) can lead to shorter acquisition time and analog hardware simplicity by measuring the whole spectrum (including bio-impedance and ECG) simultaneously. This is realized by using a wideband stimulation signal, such as a chirp, square wave or pseudo-random sequence.

A chirp often leads to a low signal to noise ratio (SNR), as the current magnitude is spread over the whole bandwidth. A square wave is easy to generate, but it suffers from lower magnitudes at higher frequencies. Compared to these, a maximal length sequence (MLS), i.e. a pseudo random pulse sequence with an equally distributed power spectrum, maintains an even SNR throughout the entire frequency range, while still allocating sufficient magnitude to each frequency bin. Besides, the MLS signal is easy to generate. These features make the MLS stimulation source suitable for low-power wideband bio-impedance analysis or bio-impedance spectroscopy. This approach has for example been disclosed in T. Sun, D. Holmes, et al, "High speed multi-frequency impedance analysis of single particles in a microfluidic cytometer using maximum length sequences", Lab on a Chip, issue 7, pp. 1034-1040, August, 2007.

A bio-impedance spectroscopy circuit should be able to detect very small dynamic impedance variations (e.g. <0.1Ω) superimposed on a large static impedance (e.g. 10Ω-1 kΩ) across a wide frequency range (e.g. 1 kHz-100 kHz), while only using a low stimulation current (e.g. <100 uA@10 kHz).

To meet these targets, however, conventional bio-impedance spectroscopy circuits utilize wideband amplifiers (typically >100 kHz) and high-speed high-resolution ADCs, which are both power hungry components. This is because both the amplifier and the ADC must have a bandwidth at least equal to the maximum frequency of the bio-impedance spectroscopy.

In addition to the above, an ECG acquisition circuit should achieve low noise (e.g. 1 µVRMS) at low frequencies (e.g. <150 Hz), with the capability to tolerate a large electrode offset (e.g. ±300 mV). In order to minimize the mains interference, the readout circuit should also have good power supply rejection ratio (PSRR) and common mode rejection ratio (CMRR).

There is therefore a need for a power-efficient circuit for bio-impedance spectroscopy which can be implemented at low cost.

SUMMARY

According to an example embodiment, there is provided an impedance spectroscopy system for bio-impedance measurement, comprising: a signal generator for generating a signal with a broadband frequency spectrum, and generating an analog injection current from the signal, wherein the analog injection signal has a high pass frequency characteristic; an amplifier for measuring a voltage signal in response to the analog injection current and simultaneously a biopotential signal; and a processor for analyzing the voltage signal to derive a bio-impedance spectrum as well to derive further information from the biopotential signal.

This system makes use of an injection current with a high pass frequency characteristic so that the injection current increases with frequency. This compensates for the typical bio-impedance behavior which typically has a low pass characteristic. By this is meant that the impedance is greater at lower frequencies and therefore more easily measured. By reducing the injection current at lower frequencies using a high pass characteristic, the overall signal to noise ratio of the system is flattened with respect to frequency, so that a more constant signal to noise ratio is achieved during a bio-impedance spectral analysis. The system also derives further information from a biopotential signal measurement, for example the further information may comprise as ECG, electroencephalography (EEG), or electromyography (EMG) signal.

Note that the term "biopotential signal" is used to refer to a voltage signal that is directly generated from the subject, such as an ECG, EEG or EMG signal. For bio-impedance measurement, the voltage is not directly generated from the subject, but is derived from a stimulation current which then enables the bio-impedance to be determined.

The system thus provides simultaneous multi-parameter measurements using a single voltage readout channel. An ECG signal may for example be obtained simultaneously with the bio-impedance spectroscopy (BIS) information, and separated by further signal processing According to an example embodiment, the system also enables a lower bandwidth amplifier to be used, because the frequency characteristic (in particular rolling off) of the amplifier is compensated by the analog injection signal, such that the effective bandwidth of the readout circuit can be increased.

The generated signal for example comprises a wideband stimulation current source which is actuated by a pseudo-random binary sequence.

The system may comprise a digital to analog converter for generating the analog injection current from the signal. It may for example comprise a current injection circuit for injecting current in dependence on a digital input.

The signal generator may comprise a maximal length sequence generator for generating a digital maximal length sequence signal. This type of sequence has an equally distributed power spectrum. By additionally introducing a high pass characteristic, the injection signal is better adapted to the nature of the bio-impedance to be measured as well as the amplifier characteristics.

The signal generator may further comprise a (digital or analog) differentiator for applying differentiation, thereby to result in the high pass frequency characteristic. The differentiation may be digital and implemented before the digital to analog conversion. The differentiation implements the high pass characteristic and converts a two level signal into a three level signal. This may also allow the power of the analog signal to be reduced, if one of the three levels is a zero level. The analog injection signal may be a three level current signal with a zero level, a positive level and a negative level.

The signal generator may be controllable in a first mode to output a maximal length sequence and in a second mode to output a differentiated maximal length sequence. The maximum length sequence is for example used to give better signal to noise ratio at low frequencies. The first mode may also be used as a reference for the second mode.

The amplifier may comprise a current feedback instrumentation amplifier or any other type of instrumentation amplifier.

The system may comprise an analog to digital converter for converting the output of the amplifier to a digital signal. It may comprise a successive approximation analog to digital converter.

The system may comprise two electrodes for current injection and two electrodes for capture of a signal for amplification by the amplifier. However, the system may be scaled with one pair of current injection electrodes and multiple pairs of signal readout electrodes at different locations.

The analog injection current may have no component below 100 Hz and the system further comprises an ECG monitor which comprises a low pass filter at the amplifier output.

The bio-impedances changes which are of interest are caused by physiological behaviors at high frequencies. At very low frequency (<1 kHz) or at very high frequency (>1 MHz), the bio-impedance is almost constant regardless of the physiological behaviors. There are many artifacts or aggressors at low frequency during a bio-impedance measurement, such as motion artifacts, 1/f noise, mains interference (50/60 Hz) and the ECG signal, and these significantly reduce the impedance measurement accuracy. Bio-impedance is thus not measured in these frequency ranges. However, the same single readout channel may be used for ECG measurements for example.

Examples in accordance with another aspect provide a bio-impedance measurement method, comprising: generating a signal with a broadband frequency spectrum; generating an analog injection current from the signal, wherein the analog injection current has a high pass frequency characteristic; measuring voltages in response to the analog injection signal; and measuring biopotential signals from the subject; analyzing the voltages to derive a bio-impedance spectrum and analyzing the biopotential signals to obtain further information.

This method provides an impedance spectroscopy method for bio-impedance measurement in which a signal is generated with a broadband frequency spectrum, and an analog injection current is derived from the signal, wherein the analog injection signal has a high pass frequency characteristic. The voltages and biopotential signals measured provide multi-parameter analysis including bio-impedance spectrum analysis as well as biopotential analysis such as ECG or EEG and/or EMG analysis. The method may comprise: generating a digital maximal length sequence signal; applying digital differentiation; and performing digital to analog conversion, thereby to result in the high pass frequency characteristic.

BRIEF DESCRIPTION OF THE FIGURES

Examples are described with reference to the accompanying drawings, in which:

FIG. 3 shows the injection current source in more detail, according to example embodiments.

FIG. 4 shows the instrumentation amplifier in more detail, according to example embodiments.

FIG. 5 shows the analog to digital converter in more detail, according to example embodiments.

FIG. 10 is a graph to show how respiration tracking and ECG monitoring are performed, according to example embodiments.

FIGS. 11a and 11b are used to explain a calibration process, according to example embodiments.

DETAILED DESCRIPTION

Some embodiments provide an impedance spectroscopy system in which a signal is generated with a broadband frequency spectrum, and an analog injection current is derived from the signal. The analog injection current has a high pass frequency characteristic. An amplifier is used for measuring a voltage in response to the analog injection signal, but also containing biopotential information (e.g., ECG, EMG or EEG), from which a bio-impedance spectrum as well as other parameters may be obtained.

An amplifier is used for measuring a biopotential impedance spectrum in response to the analog injection signal.

This system makes use of an injection current with a high pass frequency characteristic so that the injection current increases with frequency. This compensates for the typical bio-impedance behavior so that the signal to noise ratio of the system is more uniform over frequency.

Figure 2:
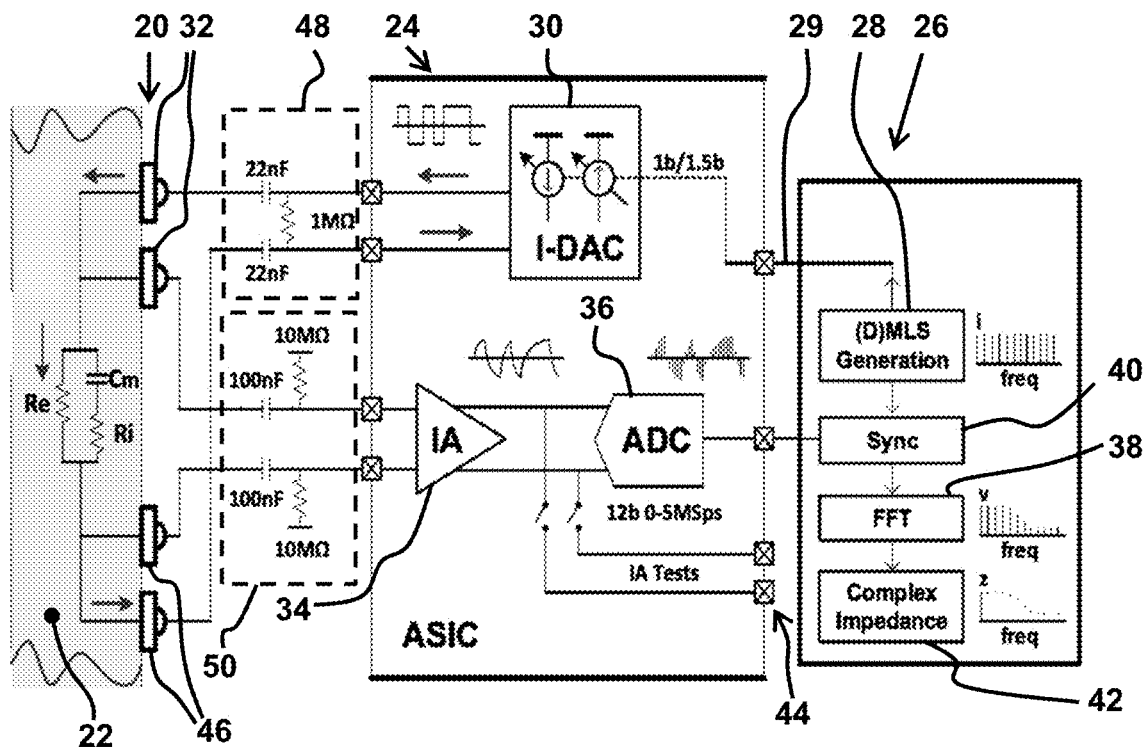
FIG. 2 shows an impedance spectroscopy system, according to example embodiments.

FIG. 2 shows an example of an impedance spectroscopy system for bio-impedance measurement. The system comprises an electrode array 20 for application to tissue 22 to be analyzed. There is a further electrode (now shown) for grounding the tissue 22. A first signal processing portion 24 is provided on chip (as an application specific integrated circuit, ASIC) for locally processing the signals delivered to and captured from the tissue. It implements analog signal processing and analog to digital conversion and digital to analog conversion. A second, off-chip, signal processing portion 26, for example a field programmable gate array (FPGA), is also provided for digital signal processing. The analog signals are thus kept as close to the electrode array as possible.

The second signal processing portion 26 comprises a signal generator 28 for generating a digital signal 29 with a broadband frequency spectrum. The broadband frequency spectrum for example includes the range 1 kHz to 100 kHz. The first signal processing portion 24 has a current source 30 for generating an analog injection current from the digital signal 29. Digital to analog conversion is effectively implemented by the current source 30. The analog injection current is driven so that it flows between a first pair of electrodes 32 of the electrode array 20. The analog injection current has a high pass frequency characteristic, by which is meant the current amplitude tails off at low frequencies.

The first signal processing portion has an amplifier 34 for measuring a biopotential value in response to the analog injection current. It comprises a low noise instrumentation amplifier with a variable gain, for example with three possible gain settings (e.g. G=4, 17 or 70). An analog to digital converter 36 generating a digital signal which is coupled back to the second signal processing portion 26 where digital signal processing takes place. The analog to digital converter (ADC) for example comprises a power efficient 12 bit successive approximation ADC.

The digital signal processing comprises spectral analysis using a Fast Fourier Transform (FFT) which is controlled in synchronism with the original digital signal 29 generated by the signal generator 28, by way of the sync unit 40. From the spectral analysis, a complex impedance is derived as a function of frequency, in unit 42. The magnitude and phase of the bio-impedance is thereby determined. The first signal processing unit portion also includes test terminals 44.

The example of FIG. 2 is a four-electrode system (plus ground), using two stimulation electrodes 32 for current injection, and two recording electrodes 46 for bio-impedance acquisition, and these may also be used for ECG acquisition as explained further below.

A four electrode configuration reduces the measurement error induced by electrode-tissue impedance (ETI), which is the major issue of a two electrode system in which the same electrodes are used for current injection as for signal measurement. In such a case, the electrode-tissue impedance is also measured, and thus cannot be distinguished from the bio-impedance.

However, the approach of some embodiments may also be applied to a two electrode system. Similarly, the system can be extended to include multiple pairs of recording electrodes and associated amplifiers but with a shared pair of current injection electrodes.

An external floating high pass filter 48 (1 MΩ and 22 nF) at the current source output blocks any DC current flowing to the tissue 22, while another high pass filter 50 (10 MΩ and 100 nF) provides biasing to the amplifier and blocks electrode offset to prevent saturation of the readout circuit.

In one example, the digital signal 29 comprises a maximal length sequence (MLS). This has a flat frequency spectrum. In order to implement the high pass frequency characteristic explained above, the current source 30 supports two modes of operation. A first mode is the standard MLS mode, and a second (new) mode is a differentiated MLS mode (which will be termed "DMLS"). The differentiation is implemented in the digital domain in the second signal processing portion 26.

In normal MLS mode, the current source 30 outputs 1-bit MLS current pulses with magnitude ±Iref. The MLS sequence has frequency components at $fsk/(2n-1)$, where fs is the MLS sampling frequency, n is the MLS order and $0 \le k \le 2n-1$. Thus, by simply choosing the MLS sample rate fs and the MLS order n, the stimulated bandwidth and the number of frequency points can be selected conveniently in the digital domain. The magnitude of the MLS current (Iref) can be set in a range of 1-100 μApp, where "pp" denotes peak to peak, and results in uniformly spread frequency components with equal magnitude, due to the properties of MLS.

Figure 1A:
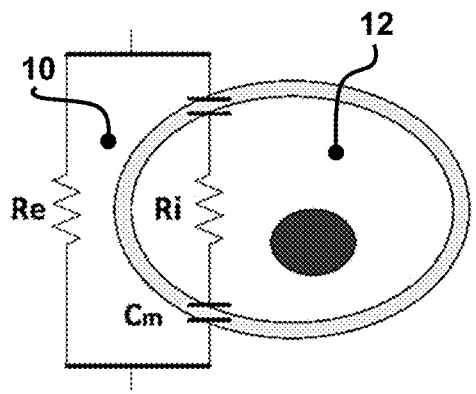
FIGS. 1a and 1b show a model of the impedance of a cellular organism and the currents flowing, according to example embodiments.
Figure 1B:
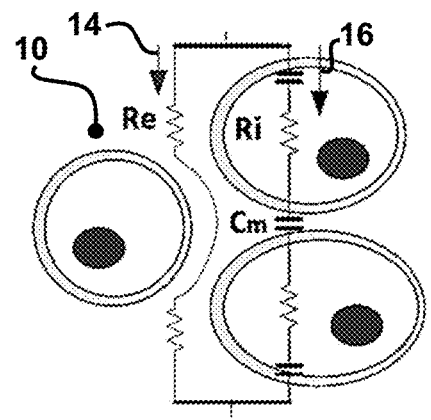

The bio-impedance is typically measured at high frequencies (10 kHz-100 kHz) where current starts penetrating into the cell as shown in FIG. 1. The dynamic bio-impedance (0.1Ω-10Ω) at high frequencies can be several orders of magnitude less than the baseline static bio-impedance (10Ω-1 kΩ). To accommodate this very large dynamic range, the voltage gain of the amplifier should be limited and a high-resolution ADC 36 is normally required, resulting in increased power consumption.

To mitigate this tradeoff, the current source 30 is configurable to the differentiated DMLS mode, where a digital differentiator $(1-Z^{-1})/2$ is applied to the normal MLS before the actual digital to analog conversion (as implemented by the current source 30), resulting in the desired high pass frequency characteristic. The current source 30 is in this way adjusted to support tri-level outputs: ±Iref and 0. It may be considered to have a 1.5 bit output. The DMLS compensates for the bio-impedance behavior that tends to have a low-pass frequency characteristic.

In this way, the DMLS improves sensitivity at higher frequencies and relaxes the dynamic range requirements, thus saving power. Furthermore, the DMLS spectrum has low current magnitudes at low frequencies, which complies with bio-excitation limits that restrict low-frequency excitation current to the body. On the other hand, the DMLS spectrum has a higher magnitude at high frequencies, which compensates the bandwidth roll-off of the instrumentation amplifier and improves the signal to noise ratio above the bandwidth of the amplifier.

FIG. 3 shows the current source 30. It comprises a current source 60 and a switching arrangement 62 for coupling the current source to the two excitation electrodes 32 in the two possible current flow directions. The current source is connected to one of the excitation electrodes by one switch and the other is connected to one of a pair of power supply terminal 33 by another switch. In the DMLS mode, there is another branch 63 for providing a zero current level.

FIG. 4 shows an example of instrumentation amplifier circuit. It uses a current feedback architecture, for example as described more fully in R. F. Yazicioglu, P. Merken, et al., "A 60 µW 60 nV/√Hz Readout Front-End for Portable Biopotential Acquisition Systems," IEEE J. Solid-State Circuits, pp. 1100-1110, May 2007. A transconductance input stage 70 converts the input voltage into current, which is mirrored to a transimpedance (TI) stage 72 and converted to the output voltage via an output resistor Ro. As a result, the instrumentation amplifier gain is determined by a ratio of an output resistance to an input resistance, Ro/Ri. By making the input resistance Ri programmable, for example from 10 kΩ to 175 kΩ, and Ro fixed, for example to 700 kΩ, there is a variable gain setting of 4, 17 and 70, while maintaining a constant bandwidth.

The maximum input dynamic range is determined by Ri·Ib, which is 15 mV at the highest gain of 70. On system level, thanks to a calibration resistor measurement (discussed further below) and the DMLS mode, bio-impedance measurements up to 125 kHz are possible, well beyond the bandwidth of the amplifier of 35 kHz in this example.

FIG. 5 shows the analog to digital converter 36 in more detail. It comprises an asynchronous successive approximation (SAR) ADC. It is for example similar to the design described in P. Harpe, et al., "A 7-to-10 b 0-to-4 MS/s flexible SAR ADC with 6.5-16 fJ/conversion-step", Digest ISSCC pp. 472-474, February 2012, but features a higher resolution of 12 b, and a higher sampling rate (0-5 MS/s). As a result of the dynamic circuitry, its power consumption scales proportionally to the sampling rate to accommodate system configurability. The internal DAC 80 for example utilizes a monotonic switching scheme and metal finger capacitors of 0.5 fF to save power and chip area. Further, redundancy in the DAC and a 2-mode comparator 82 are used to tolerate DAC settling and comparator decision errors, leading to further power reduction. On system-level, the small overall input capacitance of 1 pF relaxes the driving requirements for the amplifier while maintaining a sufficiently low kT/C sampling noise in the ADC.

Figure 6:
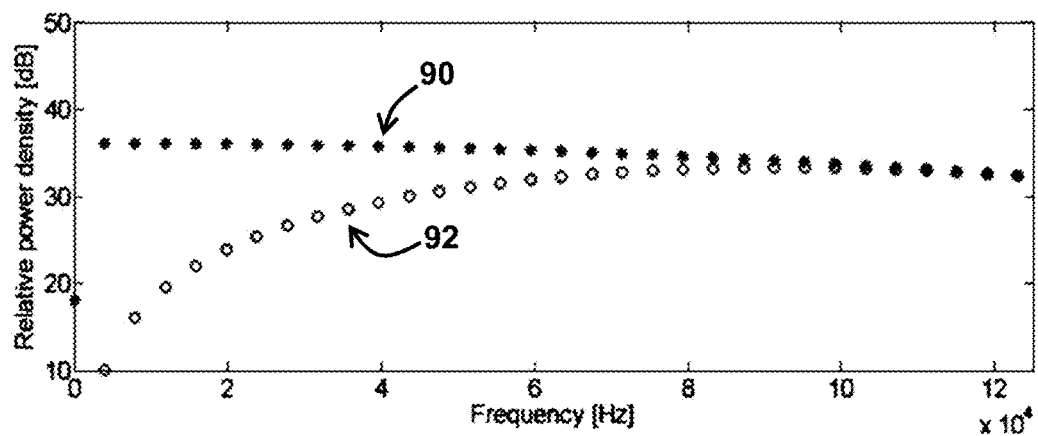
FIG. 6 shows the high pass frequency characteristic applied to the analog injection current, according to example embodiments.

FIG. 6 shows an MLS spectrum as plot 90 and a differentiated MLS spectrum (i.e. the DMLS signal as explained above) as plot 92, both for a 6th order sequence with fs=250 kHz and with an identical injection current Iref. At low frequencies, the high-pass characteristic of the DMLS results in about 25 dB less energy than MLS. This may reduce the precision for DMLS at low frequencies. For higher frequencies, the DMLS has similar energy compared to the MLS as expected. The slow roll-off at higher frequencies for both signals is due to the DAC's sinc function. The high-pass function of the DMLS signal means that a higher injection current Iref could be used to improve the measurement performance while still meeting the low frequency current stimulation regulations.

In the digital second signal processing portion 26, the measured bio-impedance spectrum is normalized to data obtained from a reference resistor measurement. In this way, all gain, phase and frequency dependencies of the entire system can be compensated and a higher measurement accuracy and bandwidth can be obtained.

Since bio-impedance is usually measured above 1 kHz, the injected MLS signal can be adjusted to only contain energy above 1 kHz (or only above a lower threshold such as 300 Hz or 100 Hz). In that way, the readout circuit can simultaneously measure a low-frequency ECG signal and a high-frequency bio-impedance signal. Furthermore, the time-variance of the measured bio-impedance can also acquire respiration simultaneously.

Figure 7:
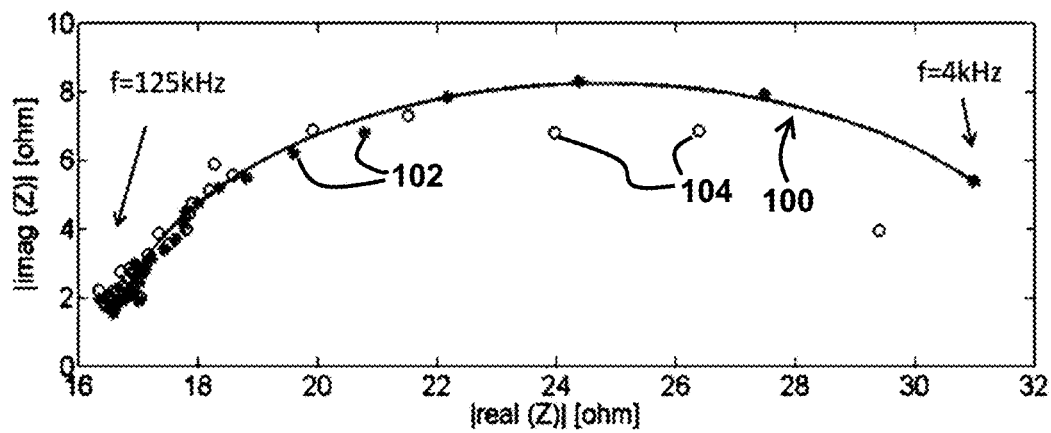
FIG. 7 shows the measured impedance as a function of frequency, according to example embodiments.

FIG. 7 shows the Cole-Cole plot of an ideal RC bio-impedance model (as shown in FIG. 1A) as plot 100 and shows the MLS and DMLS based measurements. The solid circles 102 show the MLS measurements and the open circles 104 show the DMLS measurements. For the bio-impedance, Ri=33Ω, Re=33Ω and Cm=220 nF are selected as typical bio-impedance values measured on chest. A 250 kS/s 6th-order MLS/DMLS stimulation current is used to cover a wide frequency range from 4 kHz to 125 kHz, and 50 µApp current is selected for precision.

The ADC 36 is sampled at 2 MS/s and a reference measurement uses a 33Ω resistor. For compensating gain, phase and frequency dependencies as mentioned above.

The MLS-based measurement confirms that the circuit is able to capture complex impedances over a wide frequency range. The DMLS-based measurement shows less precision at low frequencies because the stimulation current is about 25 dB lower compared to MLS (as seen in FIG. 6). However, the DMLS has similar performance as the MLS above 20 kHz, while injecting much less low-frequency current. The measurement time is only 125 ms (including averaging 256 measurements for noise reduction), and the power consumption of the first signal processing portion 24 (implemented as an ASIC) is 155 µW, including 91 µW from the current source DAC 30, 12.6 µW for the amplifier 34 and 51 µW for the ADC 36 sampling at 2 MS/s.

The DMLS mode of operation is used for high frequency measurement with low current injection, while the MLS mode is used for low frequency measurement for better accuracy, or when the current injection amplitude is not limited.

When input signal is large, the gain of the instrumentation amplifier is desired for the best use of the output dynamic range. For example ECG measured at the chest has a larger amplitude (about 5 mV) than measured at wrist (about 1 mV), while the bio-impedance measured between wrists (about 100 Ohm) is higher than measured at the wrist (about 10 Ohm). For this reason, the amplifier gain is adjustable between a set of values. This example has three different gain settings, but this is merely by way of example.

Figure 8:
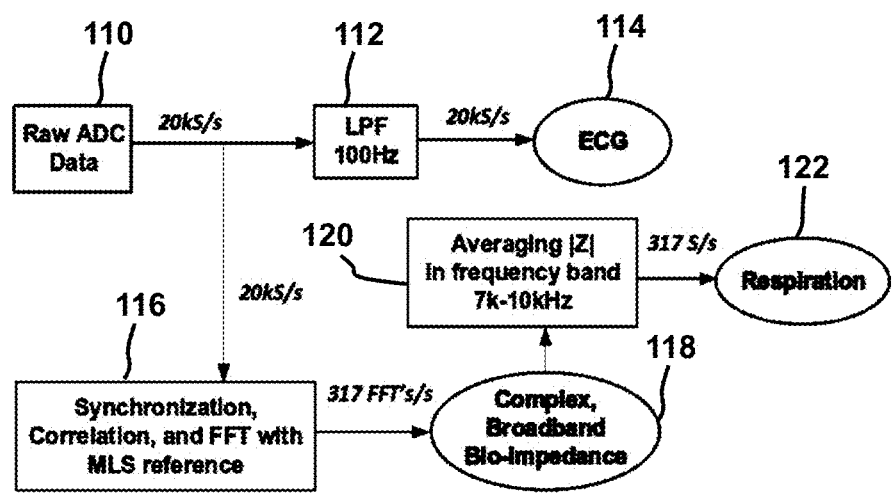
FIG. 8 shows how the system may perform simultaneous ECG monitoring, bio-impedance measurement and respiration tracking, according to example embodiments.

To record ECG and respiration simultaneously in-vivo, a data extraction process as shown in FIG. 8 may be used.

The raw data is delivered by the ADC 36 in step 110 for example at 20 k samples per second. A 6th-order 10 µApp DMLS current is for example used for long-term and low power stimulation. The lowest AC component of this signal is at 317 Hz to avoid overlap with the ECG. The ECG is recovered after a 100 Hz low pass filtering step in step 112. The filtered signal is used for ECG monitoring in step 114.

The same raw data undergoes the processing of the second signal processing portion 26, namely the synchronization, correlation and FFT analysis using the DMLS signal as the reference. This is all shown as step 116. The construction of the bio-impedance spectrum is shown as step 118.

The bio-impedance is derived from correlation with the DMLS reference signal, resulting in one FFT per MLS sequence (317 FFTs/s). Respiration is derived from bio-impedance modulation at high frequencies. Averaging over a range 7 k-10 kHz is performed in step 120 so that the slower respiration variations remain, before extracting the respiration information in step 122.

Figure 9:
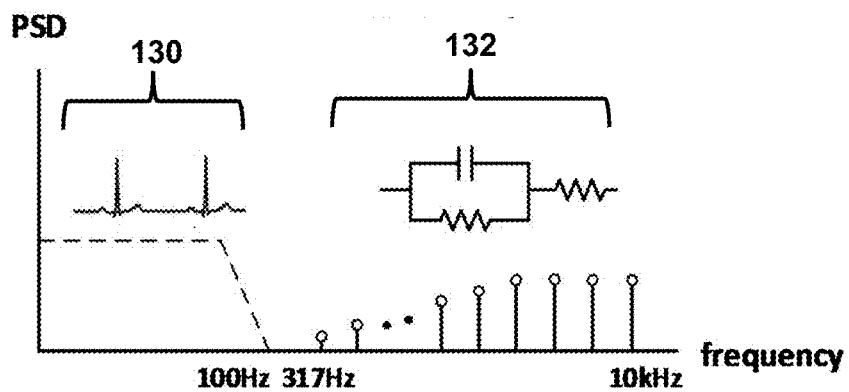
FIG. 9 shows how an ECG signal and bio-impedance signal of interest occupy different frequency bands, according to example embodiments.

FIG. 9 shows the power density spectrum (PSD) of the captured signal. The ECG signal occupies a lower bandwidth region 130 and the bio-impedance signal occupies a higher bandwidth region 132. The two measurements are taken at the same time, but located at different bandwidth. The separation of two types of signals is performed in the digital domain when all the signals are digitized, using digital low pass filter 112.

FIG. 10 shows the simultaneous recording of ECG and respiration, where stimulation electrodes were placed on the left and right wrists, and two recording electrodes were laced on the chest. Bio-impedance variation (2 Ωpp) due to respiration and ECG are detected simultaneously. The top plot shows the modulus of the measured impedance (as averaged over the frequency range 7 kHz to 10 kHz) and the bottom plot shows the ECG signal. The effect of the ECG waveform can also be seen in the top respiration plot.

The system thus provides a single channel output (the 20 kS/s digital signal) which is then processed to provide multi-parameter analysis. One example is given of ECG signals and biopotential signals. Another example is EEG signals, in which biopotentials are measured on the scalp. These biopotential signals may for example be analyzed to determine the biospectral index (BIS) which is used for determining the depth of anesthesia.

The system described above has been implemented, and the performance and results will now be outlined. At the highest gain of 70, the amplifier achieved 40 $nV/\sqrt{Hz}$ input referred noise density above 1 kHz, corresponding to a 40 $m\Omega/\sqrt{Hz}$ sensitivity (with 1 μA excitation current at each MLS frequency). In the bio-impedance measurement mode, the amplifier is only connected to the on-chip ADC, which has only 1 pF input capacitance. The amplifier consumed 7.3 μA current and has CMRR and PSRR (including the external high pass filter) of 62 dB and 75 dB, respectively. At 1.8V supply, the ADC achieves a 10.4 b effective number of bits (ENOB) for input signals up to 50 kHz and sampling rates of 100 kS/s and 5 MS/s. For higher input frequencies, the ENOB gradually degrades. The power consumption of the ADC scales linearly with the sampling rate up to 128 μW at 5 MS/s and down to 8 nW leakage power. At 100 kS/s, the achieved Figure of Merit (FoM) was 20 fJ/conversion-step.

When implementing the system of FIG. 8, the overall power consumption was 31 μW, including 18.1 μW from the current source DAC, 12.6 μW for the amplifier and 0.5 μW for the ADC sampling at 20 kS/s.

It has thus been demonstrated that the approach described above is able to measure bio-impedance from 1Ω to 10 kΩ with a 0.1Ω resolution, and covers a frequency range up to 125 kHz. In addition, the realized implementation of the system can simultaneously record ECG and respiration while consuming only 31 μW from a 1.8V supply.

As mentioned above, a calibration process, as shown in FIG. 11, prior to real bio-impedance measurement enables better measurement accuracy. During the calibration, a well-defined test resistor (or more generally impedance) Rref is first measured as a reference as shown in FIG. 11A. This gives rise to a test frequency response shown as 140. After this, the bio-impedance is measured as shown in FIG. 11B giving the frequency response shown as 142.

The calibration compensates the non-ideal transfer function of the system, including the current source digital to analog converter, the bio-impedance electrode interface and the readout channel. The calibration involves setting the product of the measured impedance spectrum with the actual impedance spectrum as a constant. This product is known from the analysis of the known reference impedance.

Calibration with a resistor and MLS/DMLS stimulation enables a frequency range beyond the instrumentation amplifier bandwidth, leading to a low power system. In long-term measurements, power can be saved in the DAC and ADC by trading measurement speed or precision, as a result of the digital configurability.

Some embodiments have been described above as implementing an MLS sequence. However, other pseudo noise sequences may be shaped to provide the desired high pass frequency characteristic. This may be achieved by implementing digital weighting or analog signal transformation (using a high pass filter).

In the example above, a first order filter may be used to generate the MLS sequence, and digital differentiation implements the high pass frequency characteristic. However a higher order digital filter may be used to generate a shaped sequence thereby implementing the high pass frequency characteristic at source. Instead of a pseudo-random sequence, a broad frequency spectrum signal may be implemented based on a chirped signal. One example of DAC, ADC and instrumentation amplifier has been given above. Certain embodiments can be applied with any DAC, ADC and amplifier design, and the above detailed implementation is purely by way of example.

The high pass frequency characteristic of the injection current may have a smooth function with respect to frequency as shown in FIG. 6, but it may also be stepped. For example a chirped signal may have discrete frequency steps, each associated with a particular current level.

High pass filtering has been shown above implemented in the digital domain. It can also be implemented in analog domain after the digital to analogue converter. In addition, the excitation signal is not only limited to MLS, other type of signals are also possible, such as multi-sine signals, where multiple-frequency sine waves with the same amplitude are injected at the same time, or a chirp, where high-pass filtering can be performed between the fmin and fmax (or the flat band) of a chirp signal.

Some embodiments allow for the simultaneous measurement of a bio-impedance spectrum as well as the analysis of biopotential information, by which is meant electrical signals generated by the body without the need for a stimulus. ECG, EEG and EMG are common non-limiting examples of information which can be derived from such biopotential signals.

Various other modifications will be readily apparent to those skilled in the art.

What is claimed is:

1. An impedance spectroscopy system for bio-impedance measurement, comprising:
   a signal generator configured to generate a signal with a broadband frequency spectrum and to generate an analog injection current from the signal with the broadband frequency spectrum, wherein the analog injection current is filtered by a high-pass filter so that the analog injection current has a high-pass frequency characteristic, and wherein the analog injection current has a greater magnitude at higher frequencies than at lower frequencies according to the high-pass frequency characteristic;

an amplifier configured to measure a voltage signal in response to the analog injection current and to simultaneously measure a biopotential signal, wherein the amplifier comprises a low-noise instrumentation amplifier with a variable gain;

a processor configured to analyze the voltage signal to derive a bio-impedance spectrum as well to derive further information from the biopotential signal; and an additional high-pass filter, wherein the additional high-pass filter is configured to provide biasing to the amplifier and prevent saturation.

2. The impedance spectroscopy system according to claim 1, further comprising a digital to analog converter configured to generate the analog injection current from the signal with the broadband frequency spectrum, wherein the signal generator comprises a pseudo-random sequence generator, wherein the high-pass filter comprises a differentiator configured to apply differentiation to result in the high-pass frequency characteristic, wherein the differentiator comprises a digital differentiator configured to apply digital differentiation before a digital to analog conversion, wherein the signal generator is controllable in a first mode to output a maximal length sequence and in a second mode to output a differentiated maximal length sequence, and wherein the maximal length sequence has a flat frequency spectrum.

3. The impedance spectroscopy system according to claim 1, wherein the variable gain comprises three possible gain settings.

4. The impedance spectroscopy system according to claim 3, wherein the three possible gain settings comprise gains of 4, 17, and 70.

5. The impedance spectroscopy system according to claim 1, wherein the high-pass filter comprises a 22 nF capacitor and a 1 MΩ resistor, and wherein the additional high-pass filter comprises a 100 nF capacitor and a 10 MΩ resistor.

6. The impedance spectroscopy system according to claim 1, wherein the analog injection current is a three level current signal with a zero level, a positive level, and a negative level, and wherein the broadband frequency spectrum is based on a chirped signal.

7. The impedance spectroscopy system according to claim 1, wherein the high-pass filter comprises a digital filter having an order greater than first order.

8. The impedance spectroscopy system according to claim 1, further comprising an analog to digital converter configured to convert an output of the amplifier to a digital signal, wherein the analog to digital converter comprises a power-efficient 12-bit successive approximation analog to digital converter.

9. The impedance spectroscopy system according to claim 8, wherein the power-efficient 12-bit successive approximation analog to digital convertor is configured to sample up to 5 MS/s, wherein the power-efficient 12-bit successive approximation analog to digital convertor uses a monotonic switching scheme and metal finger capacitors, and wherein the power-efficient 12-bit successive approximation analog to digital convertor comprises a 2-mode comparator.

10. The impedance spectroscopy system according to claim 1, further comprising two electrodes for current injection and two electrodes for capture of a signal for amplification by the amplifier.

11. The impedance spectroscopy system according to claim 1, wherein the analog injection current has no component below 100 Hz, and wherein the impedance spectroscopy system further comprises an electrocardiography (ECG) monitor that comprises a low pass filter at an output of the amplifier.

12. A bio-impedance measurement method, comprising:
generating a signal with a broadband frequency spectrum;
generating an analog injection current from the signal,
filtering the analog injection current, using a high-pass filter, so that the analog injection current has a high-pass frequency characteristic, wherein the high-pass filter comprises a digital filter having an order greater than first order, and
wherein the analog injection current has a greater magnitude at higher frequencies than at lower frequencies according to the high-pass frequency characteristic;
measuring voltages in response to the analog injection current;
measuring biopotential signals from a subject simultaneously;
analyzing the voltages to derive a bio-impedance spectrum; and
analyzing the biopotential signals to obtain further information.

13. The bio-impedance measurement method according to claim 12, further comprising:
generating a digital maximal length sequence signal;
applying digital differentiation; and
performing digital to analog conversion to result in the high-pass frequency characteristic.

14. The bio-impedance measurement method according to claim 13, further comprising:
generating, in a first mode, a maximal length sequence; and
generating, in a second mode, a differentiated maximal length sequence.

15. The bio-impedance measurement method according to claim 12, wherein the analog injection current has no component below 100 Hz, and the bio-impedance measurement method further comprises electrocardiography (ECG) monitoring by low pass filtering an amplifier output.

16. The bio-impedance measurement method according to claim 12, wherein generating the analog injection current from the signal comprises generating a pseudo-random sequence.

17. The bio-impedance measurement method according to claim 12, wherein filtering the analog injection current comprises applying digital differentiation before a digital to analog conversion to result in the high-pass frequency characteristic.

18. The bio-impedance measurement method according to claim 12, wherein measuring the voltages in response to the analog injection current and measuring the biopotential signals from the subject simultaneously is performed by an amplifier.

19. The bio-impedance measurement method according to claim 18, further comprising converting an output of the amplifier to a digital signal.

20. A bio-impedance spectroscopy circuit for bio-impedance measurement, comprising:
a signal generator configured to generate a signal with a broadband frequency spectrum and to generate an analog injection current from the signal with the broadband frequency spectrum, wherein the analog injection current is filtered by a high-pass filter so that the analog injection current has a high-pass frequency characteristic, and wherein the analog injection current has a greater magnitude at higher frequencies than at lower frequencies according to the high-pass frequency characteristic;

an amplifier configured to measure a voltage signal in response to the analog injection current and to simultaneously measure a biopotential signal;

a processor configured to analyze the voltage signal to derive a bio-impedance spectrum as well to derive further information from the biopotential signal; and an additional high-pass filter, wherein the additional high-pass filter is configured to provide biasing to the amplifier and prevent saturation.

* * * * *